(12) United States Patent
Xie et al.

(10) Patent No.: US 8,304,399 B2
(45) Date of Patent: Nov. 6, 2012

(54) HEDGEHOG SIGNALING PATHWAY PROTEINS AND USES THEREOF

(75) Inventors: Jingwu Xie, League City, TX (US); Tao Sheng, Galveston, TX (US); Xiaoli Zhang, League City, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 379 days.

(21) Appl. No.: 12/448,655

(22) PCT Filed: Nov. 9, 2007

(86) PCT No.: PCT/US2007/023671
§ 371 (c)(1),
(2), (4) Date: Dec. 14, 2009

(87) PCT Pub. No.: WO2008/060478
PCT Pub. Date: May 22, 2008

(65) Prior Publication Data
US 2010/0111955 A1 May 6, 2010

Related U.S. Application Data

(60) Provisional application No. 60/857,945, filed on Nov. 9, 2006.

(51) Int. Cl.
*A61K 31/70* (2006.01)
*C07H 21/04* (2006.01)
(52) U.S. Cl. .......................................... 514/44; 536/24.5
(58) Field of Classification Search ........................ None
See application file for complete search history.

(56) References Cited

OTHER PUBLICATIONS

Emberley et al. BMC Cancer 2002, 2:28 [online] retrieved from the internet: <URL: http://www.biomedcentral.com/1471-2407/2/280>.*
Rao et al. Journal of Biological Chemistry 2002, vol. 277, pp. 48020-48027.*

* cited by examiner

*Primary Examiner* — Tracy Vivlemore

(57) ABSTRACT

The present invention discloses a component in the hedgehog signaling pathway that can be useful in the treatment and diagnosis of hedgehog signaling pathway associated disorders. In this regard, the present invention discloses that Ran-BPM regulated the stability of hedgehog signaling molecule, smoothened (SMO) and that inactivation of RanBPM by siRNA prevented growth and metastasis of cancer cells.

2 Claims, 9 Drawing Sheets

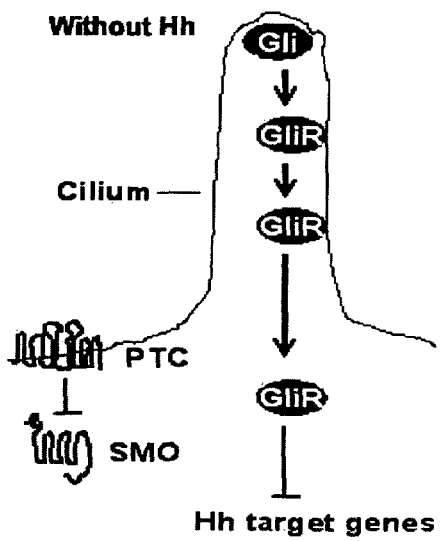
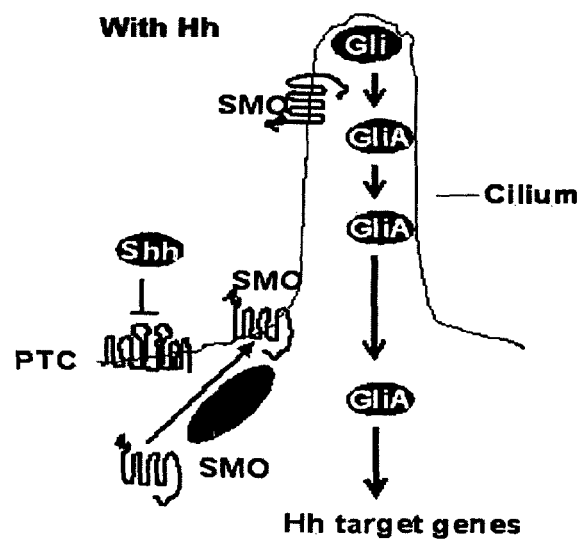
Fig. 1A  Fig. 1B
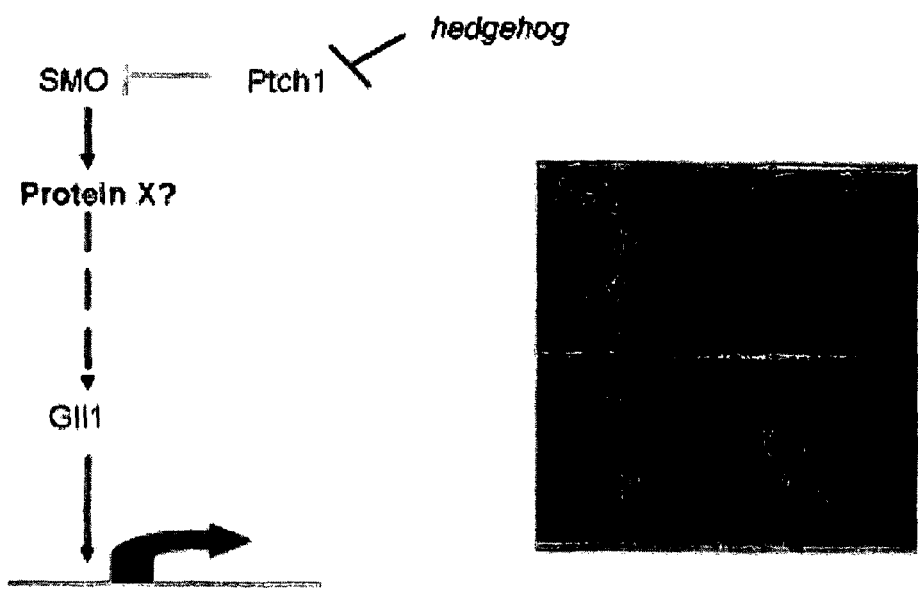
Fig. 2

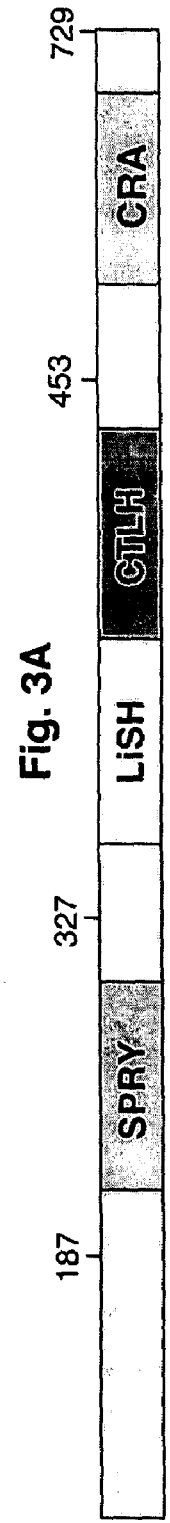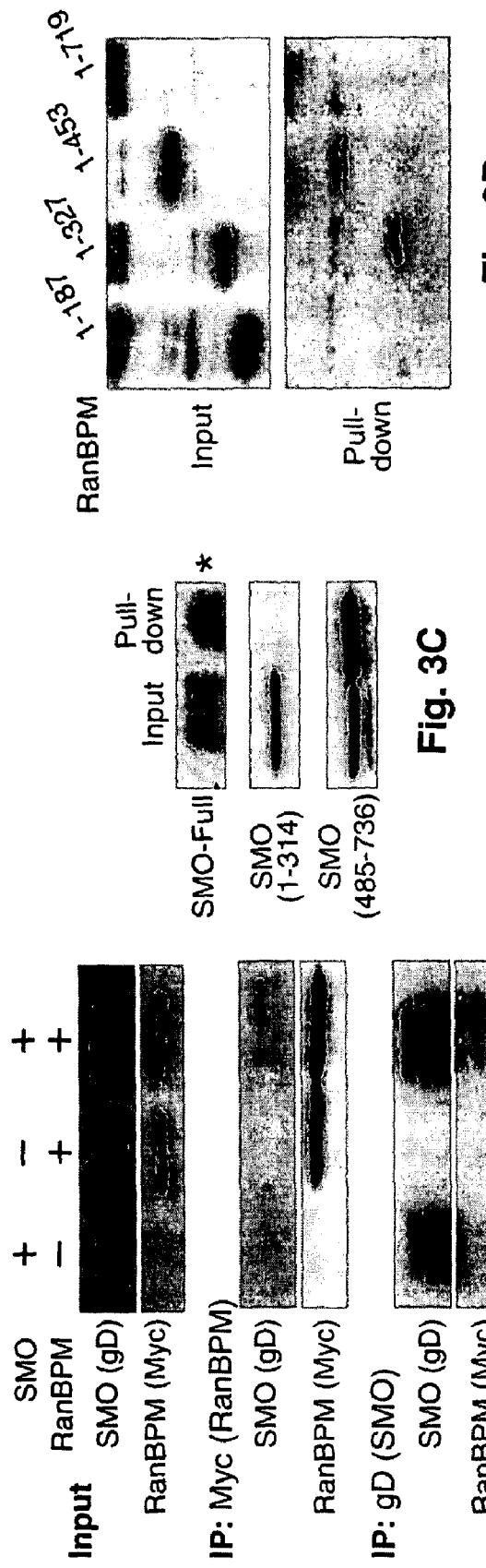
Fig. 3A
Fig. 3B
Fig. 3C
Fig. 3D

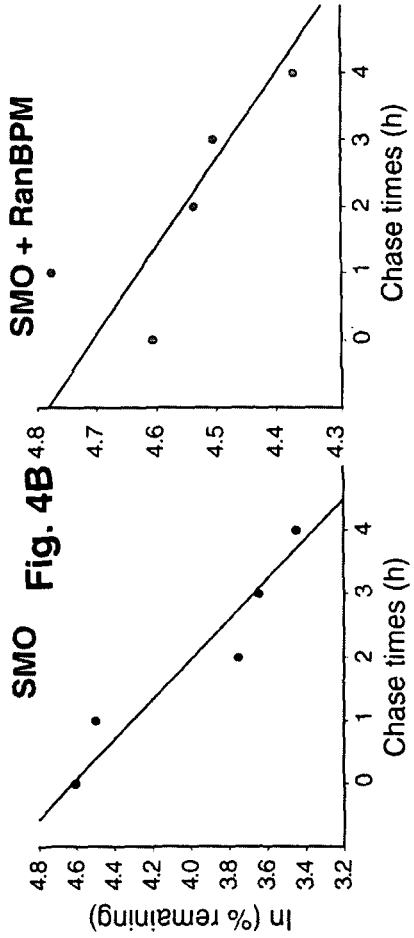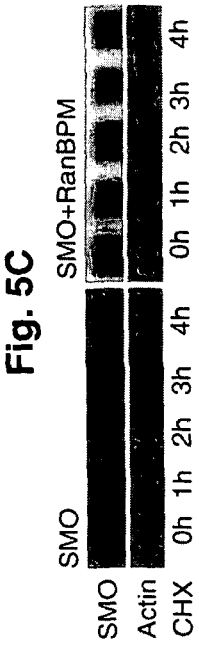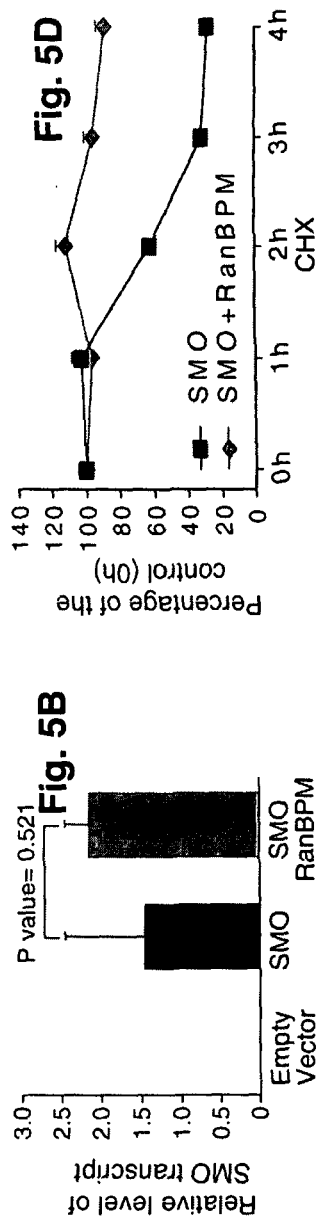

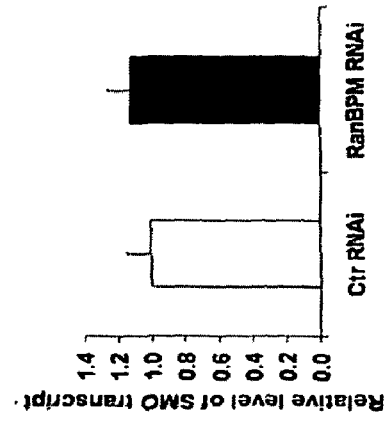
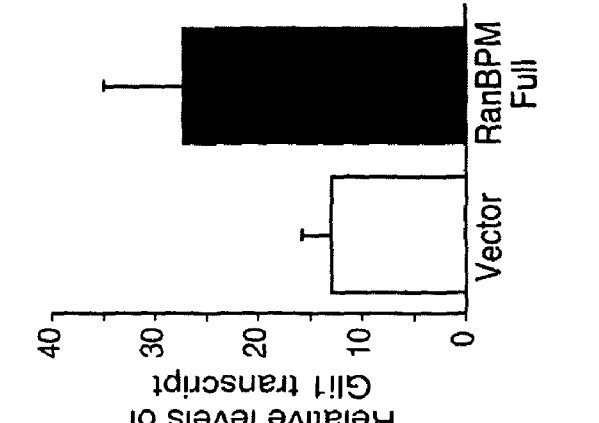
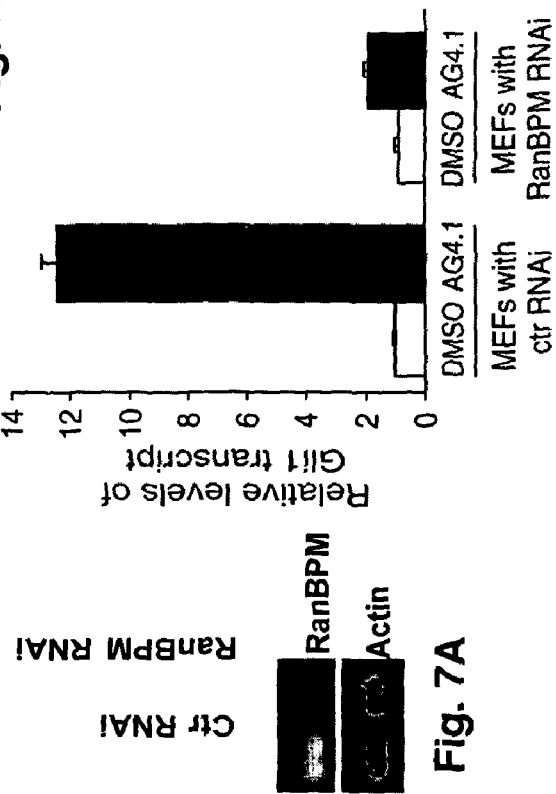

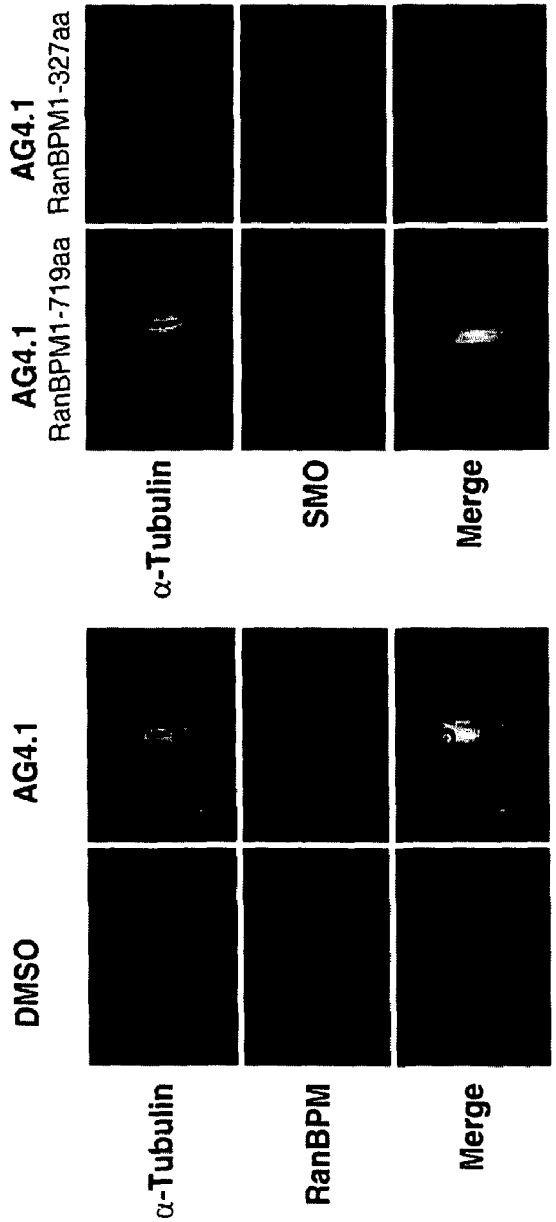

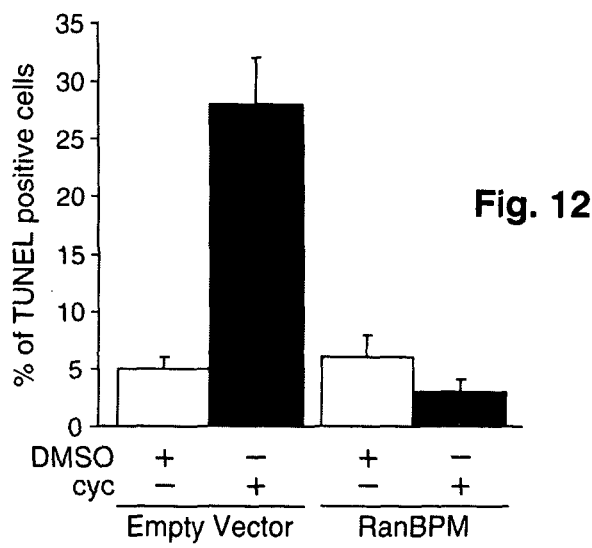
Fig. 12
Fig. 13
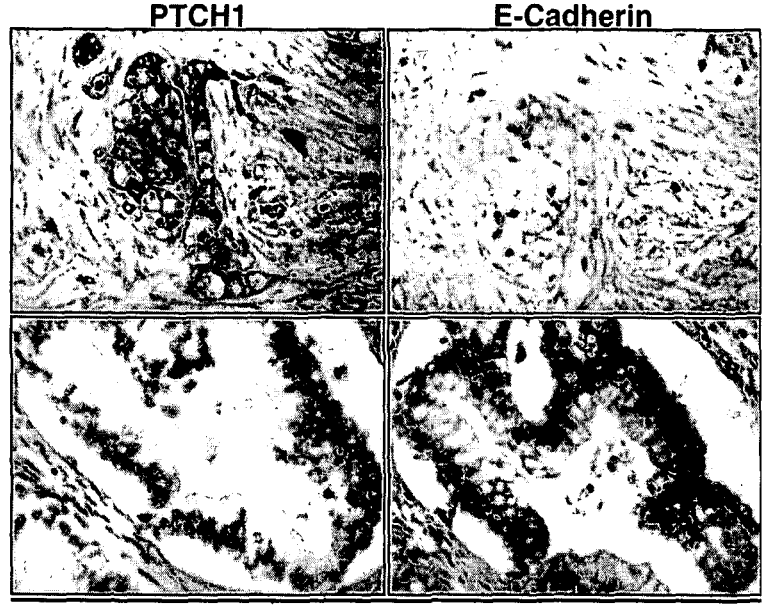
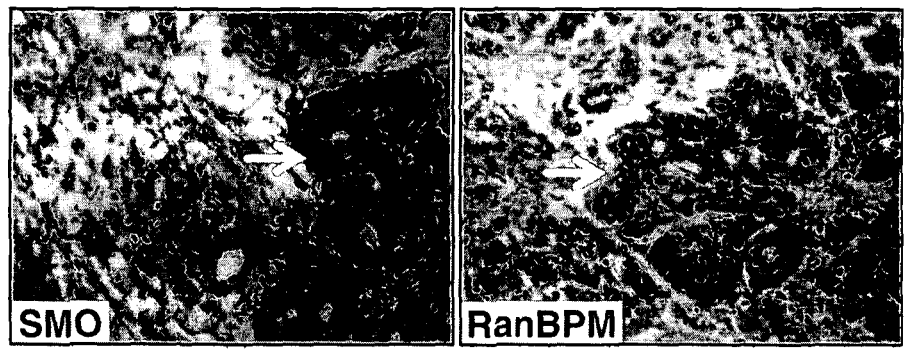
Fig. 14A    Fig. 14B

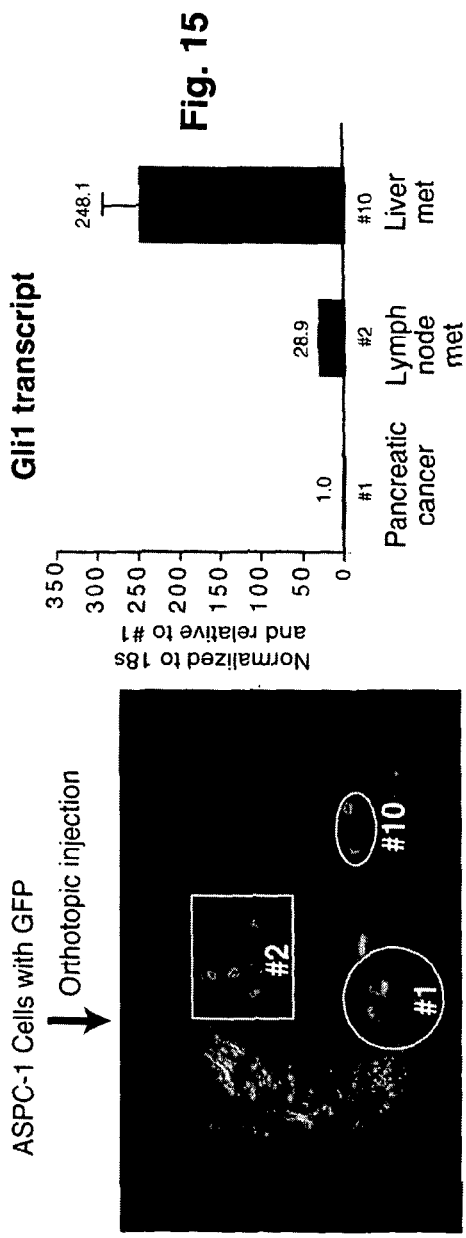

HEDGEHOG SIGNALING PATHWAY PROTEINS AND USES THEREOF

CROSS-REFERENCE TO RELATED APPLICATIONS

This is a U.S. national stage application of international application PCT/US2007/023671, filed Nov. 9, 2007, now abandoned, which claims benefit of priority of provisional application U.S. Ser. No. 60/857,945, filed Nov. 9, 2006, now abandoned, the entirety of which applications are hereby incorporated by reference.

This invention was made with government support under R01CA094160 awarded by the National Cancer Institute. The government has certain rights in the invention.

BACKGROUND OF THE INVENTION

1. Field of the Invention

The present invention relates to the field of cell signaling and treatment of cell signaling-related human disorders. More specifically, the present invention discloses a drug target for treatment of hedgehog signaling-related human disorders.

2. Description of the Related Art

The Hh pathway, originally identified in *Drosophila* (Nusslein-Volhard and Wieschaus, 1980), is important for embryonic development, tissue polarity, cell proliferation and carcinogenesis (Bale, 2002; Pasca di Magliano and Hebrok, 2003; Taipale and Beachy, 2001; Toftgard, 2000; Wetmore, 2003). Inactivation of this pathway causes developmental defects such as holoprosencephaly (Bale, 2002). Activation of this pathway is thought to be responsible for the development of almost all basal cell carcinomas (BCCs) as well as 30% of extracutaneous cancers (Xie, 2005a).

Active Hedgehog proteins are generated from precursor molecules after autoprocessing and lipid modification reactions. Hedgehog signaling proceeds with the binding of Hh ligand to the receptor PTC (Pasca di Magliano and Hebrok, 2003; Taipale and Beachy, 2001). This binding alleviates PTC-mediated suppression of SMO, thus allowing SMO to signal (Pasca di Magliano and Hebrok, 2003; Stone et al., 1996) (FIG. 1). Expression of Hedgehog appears to stabilize the SMO protein (Hooper and Scott, 2005). SMO stabilization triggers formation of a signaling complex in *Drosophila*, eventually leading to activation of the pathway (Jia et al., 2003; Lum et al., 2003; Ogden et al., 2003; Ruel et al., 2003). However, such a complex does not appear to exist in mammalian cells. SMO ultimately activates transcription factors of the Gli family. Gli molecules enter the nucleus through a nuclear localization signal (Kogerman et al., 1999; Wang and Holmgren, 1999), but little is known about the regulatory mechanism for this process. As transcription factors, Gli molecules can regulate target gene expression by direct association with a consensus binding site (5'-tgggtggtc-3') located in the promoter region of the target genes (Kinzler and Vogelstein, 1990; Sasaki et al., 1997).

The major breakthrough in the understanding of Hedgehog signaling in human cancers came from the discovery that mutations of PTC homologue 1 (PTCH1) are associated with a rare hereditary form of basal cell carcinoma—Gorlin syndrome (Epstein, 2001; Hahn et al., 1996; Johnson et al., 1996). Most of the mutations in PTCH1 lead to its inactivation, resulting in uncontrolled SMO signaling. Mice that are heterozygous for the PTC-null mutation exhibit a phenotype that resembles Gorlin syndrome (Goodrich et al., 1997; Hahn et al., 1998). Sporadic basal cell carcinomas contain mutations of PTCH1 or SMO (Lam et al., 1999; Reifenberger et al., 2005; Reifenberger et al., 1998; Xie et al., 1998). Mutant SMO, unlike the WT form, is resistant to PTC-mediated inhibition (Murone et al., 1999; Taipale et al., 2000). In basal cell carcinomas, altered hedgehog signaling leads to cell proliferation through elevated expression of PDGFRa (Xie et al., 2001), whereas targeted inhibition of hedgehog signaling causes apoptosis via Fas induction (Athar et al., 2004).

Recent data indicate that Hh signaling is activated in many types of extracutaneous tumors, including medulloblastomas, gastrointestinal, prostate, lung and breast cancers. Unlike the situation in basal cell carcinomas, overexpression of Hedgehog is believed to be responsible for altered hedgehog signaling in most of these tumors (Berman et al., 2003; Watkins et al., 2003). Transgenic mice with pancreatic-specific expression of sonic Hh (Shh) develop pancreatic tumors (Thayer et al., 2003). A subset of esophageal cancers were also found to contain genomic DNA amplification of the Shh gene (Ma et al., 2006a). Activation of the Hh pathway in gastric cancer is associated with tumor progression (Ma et al., 2005; Ma et al., 2006b), and activation of Hh signaling is detected in most metastatic prostate tumors and subsets of locally metastasized tumors (Fan, 2004; Karhadkar et al., 2004; Sanchez, 2004; Sheng et al., 2004). Activation of Hh signaling in small cell lung cancer has also been reported (Watkins et al., 2003), however, a more extensive study indicates that <10% of small cell lung cancers have activated Hh signaling (Chi et al., 2006). Recent studies also suggest that Hh signaling is activated in some breast cancers (Katano, 2005; Liu et al., 2005; Liu et al., 2006).

As a member of the 7-TM protein family, SMO shares homology with the frizzled protein family, with a cysteine-rich N-terminal extracellular domain, 7 transmembrane domains, and a cytoplasmic tail. Several small molecules are identified to associate directly with the TM domain (Chen et al., 2002a; Chen et al., 2002b; Frank-Kamenetsky Kamenetsky et al., 2002). The significance of SMO for Hh signaling in human cancer has been shown by the identification of somatic activating mutations in basal cell carcinomas and medulloblastomas (Lam et al., 1999; Reifenberger et al., 2005; Reifenberger et al., 1998; Xie et al., 1998). In the last few years, intensive studies have been performed to identify the immediate downstream molecule mediating SMO signaling. The presence of Hedgehog results in direct association of SMO with the downstream Costal-2 (Cos-2), causing the transcription factor to remain as an active form (Hooper and Scott, 2005). In contrast, no functional homologues of Cos-2 have been identified in mammalian cells (Varjosalo et al., 2006).

Other studies suggest that SMO signaling may be mediated by other molecules such as b-arrestin 2 and GRK2 (Chen et al., 2004). The unanticipated role of several intraflagellar transport (IFT) proteins in the mammalian Hh pathway indicates a functional connection between the cilia and SMO signaling (Huangfu and Anderson, 2005; Huangfu et al., 2003; Oro, 2006). Gli3 processing is significantly affected by mutations in intraflagellar transport genes (Corbit et al., 2005; Haycraft et al., 2005; Huangfu and Anderson, 2005; May et al., 2005; Olsen, 2005; Zhang et al., 2005). However, we know very little about the ciliary transport of SMO. RanBPM was initially identified as a Ran GTPase binding protein (Nakamura et al., 1998).

Thus, prior art in general, lacks the understanding of the precise involvement of hedgehog signaling pathway in carcinogenesis and other developmental defects. Specifically, prior art is deficient in the knowledge of the molecular mechanism of SMO and molecular interactions downstream of SMO and in the antagonists of the proteins of this pathway that could have substantial therapeutic importance. The present invention fulfills this long-standing need and desire in the art.

SUMMARY OF THE INVENTION

In one embodiment of the present invention, there is provided a method of inhibiting a hedgehog signaling pathway in a cell. This method comprises contacting the cell with pharmacologically effective amounts of an inhibitor of SMO-associated protein, thereby inhibiting the hedgehog signaling pathway.

In another embodiment of the present invention, there is provided a method of inhibiting SMO signaling in a cell. Such a method comprises contacting the cell with pharmacologically effective amounts of an inhibitor of SMO-associated protein. Such contact may, inter alia, prevent internalization of SMO and lysosomal degradation, prevent translocation of SMO to cilium, may inhibit DNA synthesis, inhibit cell growth, inhibit cell metastasis or a combination thereof. Thus, SMO signaling is inhibited in the cell.

In yet another embodiment of the present invention, there is provided a method of treating a pathological condition caused by altered hedgehog signaling pathway in an individual. Such a method comprises administering pharmacologically effective amounts of an inhibitor of SMO-associated protein, thereby treating the pathological condition caused by altered hedgehog signaling pathway in the individual.

In another embodiment of the present invention, there is provided a method of inhibiting SMO signaling in an individual. Such a method comprises administering pharmacologically effective amounts of an inhibitor of SMO-associated protein. Such a contact may, inter alia, prevent internalization of SMO and lysosomal degradation, prevent translocation of SMO to cilium, inhibit DNA synthesis, inhibit cell growth, inhibit cell metastasis or a combination thereof. Thus, SMO signaling in the individual is inhibited.

In yet another embodiment of the present invention, there is provided a method of diagnosing a pathological condition associated with hedgehog signaling in an individual. Such a method comprises obtaining a biological sample from the individual and determining the level of expression of a gene encoding SMO-associated protein in the biological sample, where altered expression of the gene encoding SMO associated protein indicates that the individual has a pathological condition associated with hedgehog signaling.

BRIEF DESCRIPTION OF THE DRAWINGS

FIGS. 1A-1B are diagrammatic representations of models for Hedgehog (Hh) signaling in vertebrates. FIG. 1A shows that PTC inhibits SMO signaling by promoting lysosomal degradation of SMO in the absence of Hh. Gli molecules are processed into repressor forms, which turn off the Hh signaling pathway. FIG. 1B shows that in presence of Hh, SMO-expressing endosomes segregate with PTC-expressing endosomes and recycle back to cilium by RanBPM. Gli molecules are processed to active forms (GliA) in this model, which will activate the Hh target genes.

FIG. 2 shows yeast two-hybrid screening using human SMP as bait. A total of eight clones were identified, four of which contained inserts encoding RanBPM.

FIGS. 3A-3D show detection of RanBPM-Smoothened (SMO) association. FIG. 3A shows the domain structure of RanBPM protein. The amino acid number marks the site of RanBPM mutant fragments used in FIG. 3D. FIG. 3B shows reciprocal co-immunoprecipitation of SMO with RanBPM. COS7 cells were transfected with SMO (with gD tag) and RanBPM (with MYC tag). Following IP, the immunoprecipitated proteins were tested for presence of SMO or RanBPM by Western blotting. FIG. 3C shows GST pulldown of SMO by the GST-RanBPM fusion protein, which was expressed in bacteria and purified by glutathione sepharose 4B (Amersham Pharmacia). After expression in COS7 cells, binding of SMO fragments to GST-RanBPM beads was detected by Western blotting. The cytoplasmic tail of SMO (485-736 amino acid) but not the N-terminal part of SMO (1-314 amino acid) was detected, thereby indicating that the cytoplasmic tail of SMO was responsible for RanBPM association. *indicates a band with potential SMO modifications. The GST beads alone did not pull down SMO (data not shown). FIG. 3D shows the GST pull-down of RanBPM by SMO-C-GST (SMO485-736 amino acid) fusion protein. Different fragments of RanBPM were expressed in COS7 cells, and their association with SMO was examined. It was observed that 3 RanBPM fragments, except RanBPM 1-187 amino acids, were associated with SMO-C-GST.

FIGS. 4A-4B show pulse chase analysis of SMO protein turnover in transient transfected COS7 cells. In FIG. 4A, cells were pulse-labeled with $^{35}S$ for different time points. SMO proteins were immunoprecipitated with MYC (SMO tag) antibodies and separated by SDS-PAGE. The data were obtained by quantifying the 35 S signal using a phosphoimager. FIG. 4B shows natureal log of radioactive decay of SMO protein in the presence or absence of ectopic expression of RanBPM. Data from FIG. 4A were fitted into a single exponential term by linear regression analysis, corresponding to a predicted $t_{1/2}$ of 2.2 h by SMO alone ($r_2=0.95$) and 11.2 h in the presence of RanBPM ($r_2=0.76$). This suggested that ectopic expression of RanBPM increased SMO $t_{1/2}$.

FIGS. 5A-5D show regulation of SMO stability by RanBPM. FIG. 5A shows that RanBPM stabilizes SMO, but not Gli1 in COS7 cells. FIG. 5B shows that the level of SMO transcript was not significantly altered by RanBPM expression in COS7 cells by analysing human SMO transcript by real-time PCR. FIG. 5C shows that SMO stability was by Western Blotting after adding cycloheximide (CHX, 40 μg/ml). FIG. 5D shows densitometric analysis of FIG. 5C showing that RanBPM expression increased SMO protein stability.

FIGS. 6A-6C show that inhibition of RanBPM expression decreases the endogenous SMO protein level in PLC cells. FIG. 6A shows that RanBPM expression was reduced by expression of RanBPM siRNA (10 μM). RT-PCR was used to detect RanBPM transcript. FIG. 6B shows proteins that were detected by Western Blot analysis using SMO and RanBPM antibodies (1:500 dilutions). FIG. 6C shows real time analysis of SMO transcript.

FIGS. 7A-7B show that RanBPM is involved in Hedgehog signaling. FIG. 7A shows that inactivation of RanBPM prevented SMO agonist AG4.1-mediated Gli1 expression in Hh responsive MEF cells. Following treatment of MEF cells with SMO agonist AG4.1 (10 nM for 12 hr), the level of Gli1 transcript was increased over 10 fold. In contrast, RanBPM inactivation by siRNA (RT-PCR shown in the left panel) prevented AG4.1-induced Gli1 expression. FIG. 7B shows that transfection of RanBPM plasmid into 293 cells (48 hr) was sufficient to increase the level of Gli1 transcript. Transcripts for Gli1 (FIG. 7A for mouse Gli1 and FIG. 7B for human Gli1) were detected by real-time PCR.

FIGS. 8A-8D show detection of ciliary transport of SMO and RanBPM using confocal microscope (630×). NIH3T3 cells were transfected with RanBM. Forty-eight hr later, cells were serum starved for 24 hr and treated with SMO agonist AG4.1 or DMSO for 1 hr. After fixation with 4% paraformaldehyde, cells were stained with acetylated u-tubulin Abs, RanBPM or SMO 630× for all images). SMO agonist AG4.1 induced ciliary transport of RanBPM (FIGS. 8A, 8B) and SMO (FIG. 8C). In the presence of truncated RanBPM (1-327 amino acid), SMO was not localized to the cilium (FIG. 8D).

FIGS. 9A-9B show detection of RanBPM expression in human cancer cells such as PLC/PRF/5 cells. FIG. 9A shows western blot data for RanBPM expression using rabbit polyclonal antibodies to RanBPM in PLC/PRF/5 cells. The RanBPM expression was knocked down by siRNA. FIG. 9B shows RT-PCR of RanBPM in PLC/PRF/5 cells. The RanBPm protein level was barely detected after knocking down of RanBPM in PLC/PRF/5 cells.

FIG. 10A compares BrdU labeling of PLC/PRF/5 cells that contain altered hedgehog signaling and of HepG2 cells that contain no detectable hedgehog signaling after RanBPM siRNA treatment. FIG. 10B shows percentage of BrdU positive cells in these two cell lines. The percentage of BrdU positive cells in the control group were two times higher than that in the RanBPM siRNA-treated group (20.9% vs 10.2%, P value<0.04 based on Student's t test, p value<0.05 was considered statistically significant) in PLC/PRF/5 cells. No significant change in BrdU by RanBPMsiRNa was observed in HepG2 cells, which have no detectable activated hedgehog signaling.

FIG. 12 shows that ectopic expression of RanBPM rendered PLC/PRF/5 cells resistant to cyclopamine-mediated apoptosis. PLC cells were transfected with RanBPM expression plasmid. Forty-eight hours post-transfection, cyclopamine was added to the medium for 24 hr and TUNNEL was used to detect apoptosis. The control group was treated with DMSO. RanBPM expression was detected by immunofluorescent staining. In cells without RanBPM expression, 1000 cells were counted for TUNNEL staining. Over 500 RanBPM positive cells were counted for this analysis. The experiment was repeated three times with similar results.

FIG. 13 shows that expression of Hh target gene PTCH1 is associated with e-cadherin loss in human pancreatic cancers. Immunohistochemistry was performed with antibodies to PTCH1 (Santa Cruz Cat#6149 in 1:50 dilution) and E-cadherin (BD transduction lab Cat#612130 in 1:100 dilution) using a universal quick stain kit from Vector laboratory. A significant association between PTCH1 positive tumors with loss of E-cadherin expression was observed. In these two tumors, expression of PTCH1 and E-cadherin was reversely correlated.

FIGS. 14A-14B show expression of SMO and RanBPM in pancreatic cancers. Using GST fusion proteins, polyclonal antibodies to RanBPM and SMO were generated. These antibodies were further purified by corresponding GST fusion proteins. 1:100 dilutions were used to detect SMO and RanBPM expression in cancer tissues by immunohistochemistry using the same procedure as described in FIG. 13. Positive staining is in red (indicated by arrows). FIG. 14A shows expression of SMO in tumors with PTCH1 expression and FIG. 14B shows expression of RanBPM.

FIG. 15 shows an orthotopic mouse model for pancreatic cancer metastasis. Using ASPC1 cells expressing GFP, a model for pancreatic cancer metastasis was established. $5 \times 10^4$ cells were injected into pancreas of Nu/Nu mice (n=8). 6 weeks later, tumor metastasis was visualized by whole body imaging system. GFP positive tumors from pancreas, lymph node and liver were collected for real-time PCR analysis. Expression of Hh target gene Gli1, was significantly elevated during metastasis.

FIGS. 16A-16B show that down-regulation of Gli1/2 or RanBPM reduces pancreatic cancer metastasis. AsPC1 cells were treated with either control RNAi, RanBPM RNAi or mixed RNAi for Gli1 and Gli2 before injection into pancrease. Mice were then IP-injected with corresponding RNAi twice weekly for the entire experiment (10 weeks). For each mouse, 2.5 µg of Dotap (from Roche) was mixed with 1 µg of RNAi and 10 µg RNAi was used per mouse. At the end, mice were sacrificed and tumor metastasis was detected by whole body imaging system. FIG. 16A shows that RanBPM and Gli1/2 inactivation prevented distal metastasis of pancreatic cancer (liver metastasis) using a ASPC1 subline ASPC1-lent, which is derived from lentivirus-mediated GFP expression. FIG. 16B shows that RanBPM and Gli1/2 inactivation prevented lymph node metastasis of pancreatic cancer using a ASPC1 subline ASPC1-lent, which is derived from lentivirus-mediated GFP expression. GFP-positive tumors in circles are primary tumors.

DETAILED DESCRIPTION OF THE INVENTION

Figure 10A:
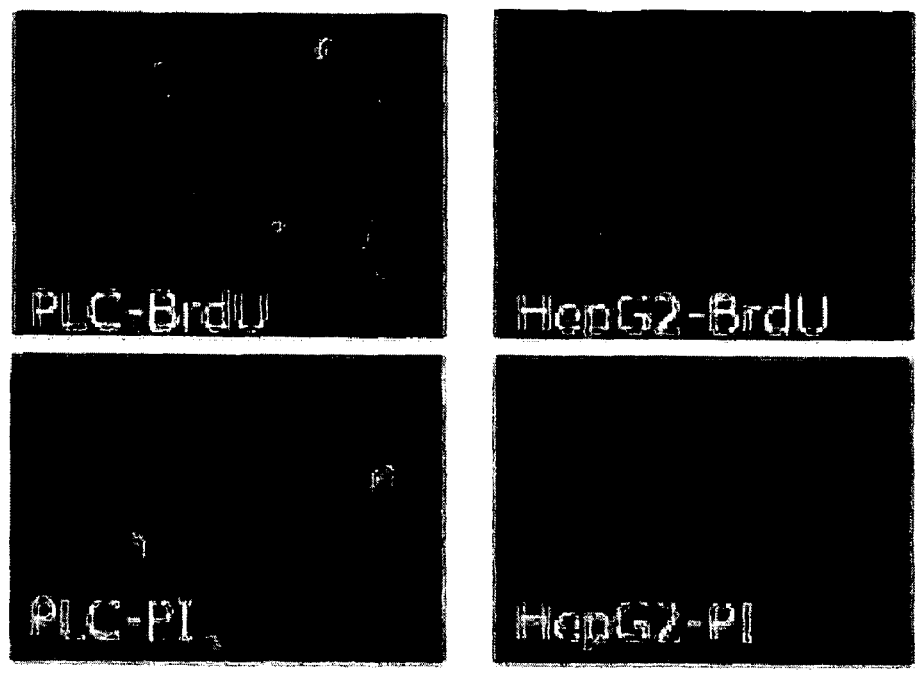
FIGS. 10A-10B show that inactivation of RanBPM significantly inhibited DNA synthesis in PLC/PRF/5 cells.

The present invention is drawn to understanding the molecular basis of hedgehog signaling (FIGS. 1A and 1B) and to determine whether inhibition of this pathway with novel small molecules attenuated hedgehog signaling driven disorders such as cancer.

In this regard, the present invention discloses a drug target in the hedghog signaling pathway that can be targeted for treatment of disorders associated with hedgehog signaling pathway. This molecule is the molecule originally identified as Ran GTPase-binding protein (RanBPM) (Nakamura et al., 1998). Endogenous protein interactions were examined to determine the molecular mechanisms by which RanBPM regulated SMO stability and translocation. Additionally, using Gst pull-down, co-immunoprecipitation and confocal microscope analyses, the protein domains responsible for interaction between RanBPM and SMO were identified. Direct protein-protein interactions between SMO and RanBPM are assessed by in vitro binding assays. Furthermore, by examining effects of ectopic expression of RanBPM and its mutant forms, or decreasing endogenous RanBPM expression by siRNA, the role of RanBPM in SMO signaling is determined in functional assays: SMO protein translocation and downstream reporter activity. These in vitro data are confirmed by assessing RanBPM functions in cancer cell lines and primary tumor specimens. It is contemplated that RanBPM inactivation may inhibit cell growth by hedgehog signaling dependent or independent mechanisms.

Using siRNA of RanBPM, the present invention demonstrated that RanBPM was required for the growth and metastasis of cancer cells with altered hedgehog signaling pathway. These data indicate that targeted inhibition of RanBPM is a novel way to treat the cancers as well as other human pathological conditions in which hedgehog signaling is implicated. Currently, there are agents available for inhibition of SMO but no agents available for targeting RanBPM or RanBP10. Thus, the data disclosed herein provides evidence for the first time that RanBPM expression can be used for early diagnosis of human cancers and other pathological conditions and that targeted inhibition of hedgehog signaling using RanBPM inhibitors should be effective in therapeutic treatment of these conditions. These human cancers may include but are not limited to basal cell carcinoma, medulloblastomas, breast, prostate, gastrointestinal (GI) and lung cancers.

The present invention is directed to a method of inhibiting hedgehog signaling pathway in a cell, comprising: contacting the cell with pharmcologically effective amounts of an inhibitor of SMO-associated protein, thereby inhibiting the hedgehog signaling pathway in the cell. Generally, the inhibitor may prevent internalization of SMO and lysosomal degradation, translocation of SMO to cilium, may inhibit DNA synthesis, may inhibit cell growth, may inhibit cell metastasis or a combination thereof. The SMO associated protein inhibited in this method is RanBPM. Example of the inhibitor may include but is not limited to siRNA, an antibody, or a small molecule inhibitor. The hedgehog signaling pathway may be inhibited in any cell including a cancer cell. Representative examples of the cancer cell may include but is not limited to a basal cell carcinoma cell, a medulloblastoma cell, a breast cancer cell, a prostate cancer cell, a gastrointestinal cancer cell, a pancreatic cancer cell or a lung cancer cell.

The present invention is also directed to a method of inhibiting SMO signaling in a cell, comprising: contacting the cell with pharmcologically effective amounts of an inhibitor of SMO-associated protein, where the contact affects internalization of SMO and lysosomal degradation, translocation of SMO to cilium, inhibits DNA synthesis, inhibits cell growth, inhibits cell metastasis or a combination thereof, thereby inhibiting the SMO signaling in the cell. The SMO associated protein inhibited by such a method may be RanBPM. Representative examples of the inhibitor may include but is not limited to siRNA, an antibody, or a small molecule inhibitor. The SMO signaling may be inhibited in a cancer cell. Representative examples of such a cancer cell may include but is not limited to a basal cell carcinoma cell, medulloblastoma cell, breast cancer cell, prostate cancer cell, gastrointestinal cancer cell, a pancreatic cancer cell or lung cancer cell.

The present invention is further directed to a method of treating a pathological condition caused by altered hedgehog signaling pathway in an individual, comprising: administering a pharmacologically effective amounts of an inhibitor of SMO-associated protein, thereby treating the pathological condition associated by altered hedgehog signaling pathway in the individual. Generally, the inhibitor may prevent internalization of SMO and lysosomal degradation, translocation of SMO to cilium, may inhibit DNA synthesis, may inhibit cell growth, inhibit cell metastasis or a combination thereof. The SMO associated protein inhibited by such a method may be RanBPM. Representative examples of the inhibitor may include but is not limited to siRNA, an antibody, or a small molecule inhibitor. The pathological condition in the individual may be cancer or a developmental defect caused by altered hedgehog signaling pathway. Representative examples of the cancer may include but is not limited to basal cell carcinoma, medulloblastoma, breast cancer, prostate cancer, gastrointestinal cancer, pancreatic cancer or lung cancer.

The present invention is still further directed to a method of inhibiting SMO signaling in an individual, comprising: administering a pharmacologically effective amounts of an inhibitor of SMO-associated protein such that said inhibitor affects internalization of SMO and lysosomal degradation, translocation of SMO to cilium, inhibits DNA synthesis, inhibits cell growth, inhibits cell metastasis or a combination thereof, thereby treating inhibiting SMO signaling in the individual. The SMO associated protein inhibited by such a method may be RanBPM. Representative examples of the inhibitor may include but is not limited to siRNA, an antibody, or a small molecule inhibitor. The individual benefiting from this method may have cancer or a developmental defect caused by altered hedgehog signaling pathway. Representative examples of the cancer may include but is not limited to basal cell carcinoma, medulloblastoma, breast cancer, prostate cancer, gastrointestinal cancer, pancreatic cancer or lung cancer.

The present invention is also directed to a method of diagnosing a pathological condition associated with hedgehog signaling in an individual, comprising: obtaining biological sample from the individual; and determining level of expression of a gene encoding SMO associated protein in the biological sample, where altered expression of the gene encoding SMO associated protein indicates that the individual has a pathological condition associated with hedgehog signaling. The SMO associated protein whose expression is determined by such a method may be RanBPM. The level of expression of the gene may be determined by in-situ hybridization or RT-PCR.

Alternatively, the gene expression may be determined at the protein level. The protein level of the gene may be determined using antibodies specific to RanBPM. The protein level of the gene may be determined by immunohistochemistry, flow cytometry or ELISA. Additionally, the biological sample may be a blood sample or a fine needle aspiration specimen. The pathological condition in the individual may be cancer or a developmental defect caused by altered hedgehog signaling pathway. Representative examples of the cancer may include but is not limited to basal cell carcinoma, medulloblastoma, breast cancer, prostate cancer, gastrointestinal cancer, pancreatic cancer or lung cancer.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

As used herein, the term "contacting" refers to any suitable method of bringing the inhibitor described herein into contact with a cell culture system. In vitro or ex vivo may be achieved by exposing the above-mentioned cell to the composition in a suitable medium.

An anti-cancer agent may be administered concurrently or sequentially with the inhibitor used herein. The inhibitor described herein, the anti-cancer agent, or combination thereof can be administered independently, either systemically or locally, by any method standard in the art, for example, orally, subcutaneously, intravenously, parenterally, intraperitoneally, intradermally, intramuscularly, topically, enterally, rectally, nasally, buccally, vaginally or by inhalation spray, by drug pump or contained within transdermal patch or an implant. Dosage formulations of the composition described herein may comprise conventional non-toxic, physiologically or pharmaceutically acceptable carriers or vehicles suitable for the method of administration and are well known to an individual having ordinary skill in this art.

The inhibitor described herein, the anti-cancer agent or combination thereof may be administered independently one or more times to achieve, maintain or improve upon a therapeutic effect. It is well within the skill of an artisan to determine dosage or whether a suitable dosage of either or both of the composition and anti-cancer agent comprises a single administered dose or multiple administered doses. An appropriate dosage depends on the subject's health, the inhibition of the hedgehog signaling, SMO signaling and/or treatment of the cancer, the route of administration and the formulation used.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Detection of RanBPM-SMO Association

RanBPM was identified as a SMO-binding protein in a yeast two-hybrid screen (FIG. 2). Briefly, the SMO-associated molecule were screened using yeast two-hybrid screening. SMO was used as a bait and the cDNA library was from Hela cells (hedgehog signaling responsive cell line). Clone#35 encodes human RanBPM (RanBP9). Another homologue of RanBPM is RanBP10. A total of eight clones were identified. Four of these contained the inserts encoding RanBPM or its homologues RanBP9 or RanBP10.

RanBPM identified herein contains several domains involved in protein.protein interactions and microtubule binding (FIG. 3A). Co-IP experiments were performed to confirm the interactions between RanBPM and SMO. RanBPM was detected after immunoprecipitation with anti-gD (SMO tag) antibodies (Abs). Conversely, SMO was detected after immunoprecipitation with anti-MYC (RanBPM tag) Abs (FIG. 3B), suggesting that SMO and RanBPM are in the same complex under this condition.

To validate the results obtained by co-IP, GST pull-down experiments were performed. Using purified GST-RanBPM fusion protein, the full-length and the cytoplasmic fragment of SMO, but not the N-terminal part were pulled down (FIG. 3C), suggesting that RanBPM associates with the cytoplasmic tail of SMO. When SMO-C-GST protein was used (SMO485-736aa), it was observed that 3 of the 4 RanBPM fragments were pulled down (FIG. 3D). This experiment supports the hypothesis that RanBPM specifically associates with SMO.

Example 2

Stabilization of SMO Protein by RanBPM

The present invention also provides evidence to suggest that RanBPM regulates the stability of SMO. Based on the pulse-chase experiment, it was estimated that SMO has a short half-life ($t_{1/2}$=2.2 h, FIGS. 4A, 4B), but RanBPM increases SMO $t_{1/2}$ by 5 fold ($t_{1/2}$11.2 h, FIGS. 4A, 4B). The data was further confirmed by protein stability analysis in the presence of cycloheximide (CHX), inhibitor for new protein synthesis (FIGS. 5A, 5C). In contrast to SMO, the stability of Gli1 was not affected by RanBPM (FIG. 5A), suggesting that RanBPM specifically stabilizes SMO protein.

Furthermore, the present invention also demonstrates that stability of endogenous SMO protein was affected in a cell line sensitive to Hh signaling inhibition. To detect endogenous proteins of RanBPM and SMO, antibodies were generated using GST fusion proteins in rabbit. Following reduced expression of RanBPM by siRNA transfection (FIG. 6A), the corresponding protein band with the expected size of RanBPM was undetectable by Western blot with RanBPM antibodies (FIG. 6B). Only a single band was detected (FIG. 6B shows the 75-150 KD region for RanBPM) in the control siRNA treated sample. In addition, a single band around the expected size of SMO was detected and the amount of SMO protein was dramatically reduced following inactivation of RanBPM (FIG. 6B shows the 100-200 KD region) although SMO transcript was not affected by RanBPM siRNA (FIG. 6C).

These results suggest that the stability of endogenous SMO protein is regulated by RanBPM. These results indicated that RanBPM specifically associated with SMO and regulated SMO protein stability and this association was regulated by Hh signaling. The biochemical analyses of RanBPM-SMP interactions will provide molecular basis for RanBPM's involvement in Hh signaling.

Example 3

Involvement of RanBPM in Hh Signaling

To examine whether RanBPM was required for SMO signaling, the SMO agonist (AG4.1)-mediated Gli1 expression was examined in Hh responsive MEF cells following treatment of RanBPM siRNA or the control siRNA. It is demonstrated herein that knocking down endogenous RanBPM expression by RNAi prevented SMO-mediated Gli1 expression in MEF cells (FIG. 7A), suggesting that RanBPM is required for SMO-mediated signaling. In addition, the present invention examined whether ectopic expression of RanBPM was sufficient to induce Hh target gene expression in 293 cells and found that expression of full-length RanBPM increased the basal level of Hh target gene Gli1 (FIG. 7B). These data indicate that RanBPM was required for Hh signaling.

Example 4

Cilium Translocation of SMO and RanBPM

Another mechanism by which RanBPM facilitates SMO signaling is by promoting SMO transport to cilium. Previously published data show SMO transport to cilium in the presence of Shh. The present invention demonstrates that RanBPM co-localized with acetylated alpha tubulin (a marker for the cilium) upon activation of Hh signaling by SMO agonist AG4.1 in NIH3T3 cells (FIGS. 8A, 8B). In addition, it was observed that expression of full-length RanBPM, but not the truncated fragment 1-327aa (RanBPM1-327), enhanced SMO transport to cilium (FIGS. 8C, 8D), suggesting that this fragment may function as a dominant negative RanBPM, and that additional protein domains are necessary for RanBPM-mediated ciliary transport of SMO. Since ciliary transport of SMO and RanBPM occurs within 1 hr following AG4.1 stimulation, the effects of RanBPM on SMO should be a direct one (vs. an indirect effect through regulation of SMO protein stability since SMO half-life is 2.2 hr).

Example 5

In vitro Effect of Knocking Down RanBPM

In order to study the function of RanBPM, antibodies to RanBPM were generated in rabbit using purified RanBPM-Gst. Specific RanBPM siRNA were purchased from Dharmacon's SMART pool and the control siRNA was purchased from Ambion's siRNA control (Cat#4624). The target sequences for the siRNA of RanBPM (RanBP9 and its homologue RanBP10) were as follows: #1. 5'-gaacaugaauagacuacca-3' (SEQ ID NO: 1); #2. 5'-ucacugaccuaccgccaaa-3' SE ID NO: 5); #3. 5'-ggaugccuuuagccuacuauu-3' (SEQ ID NO: 2). The siRNAs were introduced into cells using electroporation according to the manufacturer's instruction. After 24 hr, cells were lysed and proteins separated by 8% SDS-PAGE. Proteins were detected using antibodies to RanBPM (1:200, the final protein concentration was 0.1 µg/ml) and β-actin (Sigma).

In addition to Western Blot analysis, RT-PCR of RAnBPM was also performed in PLC/PRF/5 cells that have altered hedgehog signaling pathway. Briefly, total RNAs were extracted from cells 24 hrpost-transfection of siRNAs and RanBPM expression was examined by RT-PCR using the following primers: RanBPM forward primer-5'-ggtgatgtcattggctgttg-3' (SEQ ID NO: 3); RanBPM reverse primer-5'-ggcatcgaccacttctcctgg-3' (SEQ ID NO: 4). β-actin was used as the internal control. For antibody purification, the serum was first precipitated with ammonium persulfate and non-specific antibodies to GST were removed by GST beads. RanBPM specific antibodies were purified with RanBPM-GST beads according to a protocol by Bar-Peled and Raikhel, 1996.

It was observed herein that RanBPM was barely detectable after knocking sown of RanBPM by siRNA in PLC/PRF/5 cells (FIGS. 9A-9B). Similar observations were made in other cell lines. These results also demonstrated that the antibodies developed herein were specific to RanBPM.

Figure 10B:
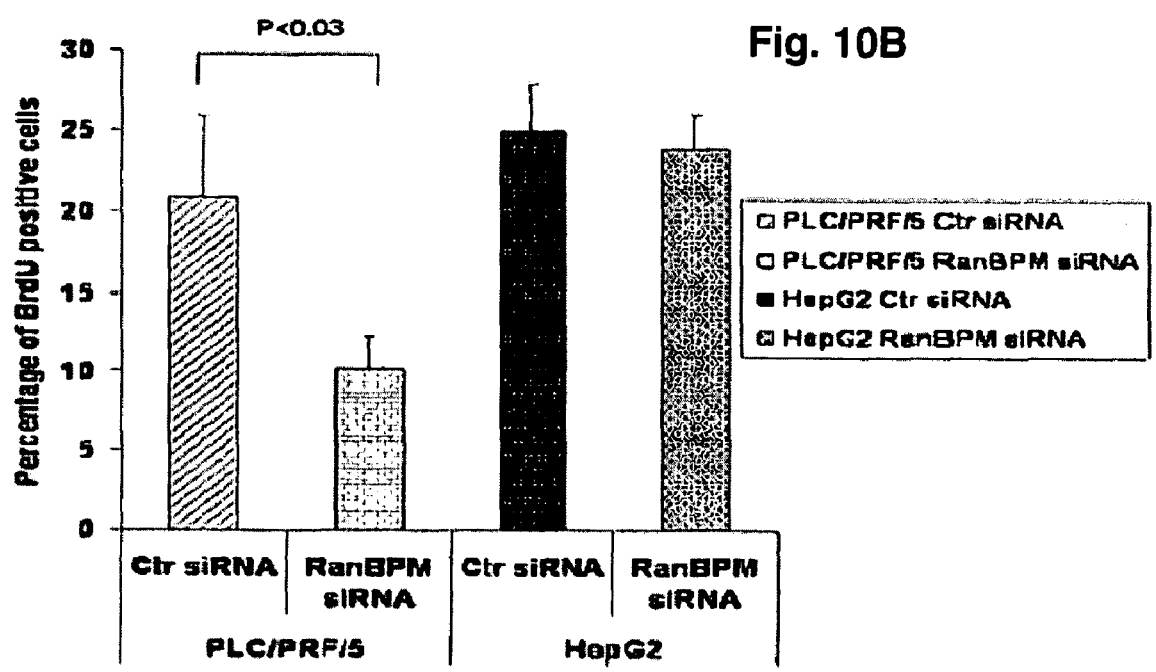

The effect of knocking down RanBPM on DNA synthesis was also examined herein. It is known that PLC/PRF/5 cells have altered hedgehog signaling whereas HepG2 cells have no altered hedgehog signaling. Thus, growth of PLC/PRF/5 cells but not HepG2 cells is dependent on hedgehog signaling. Hence, the DNA synthesis was compared in these two cells. Briefly, after transfection of siRNAs for 24 hrs, the cells were incubated with BrdU for 60 min. Brdu was detected with FITC-conjugated anti-BrdU antibodies (BD sciences, Inc.). The percentage of BrdU positive cells in the control group was two times higher than that in the RanBPM siRNa-treated group (20.9% vs 10.2%, P value<0.04 based I Student's t test, p value<0.05 was considered statistically significant) in PLC/PRF/5 cells. However, no significant change in Brdu by RanBPM siRNA was observed in HepG2 cells (FIGS. 10A, 10B).

Figure 11C:
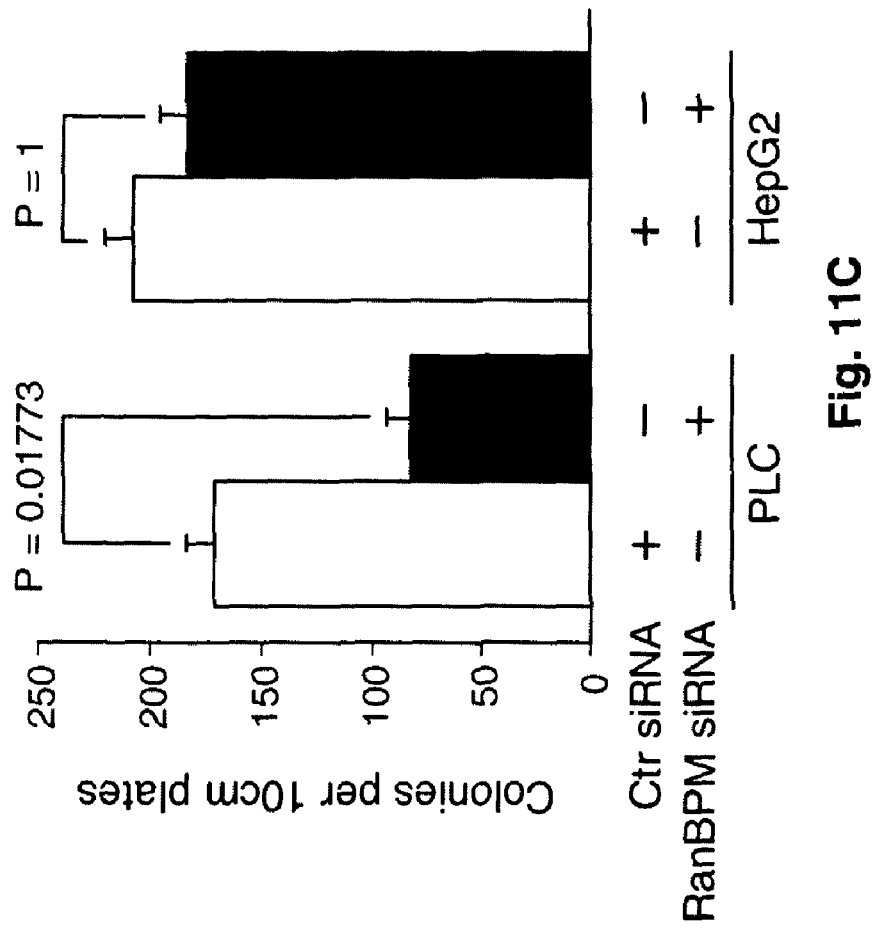
FIGS. 11A-11C show anchorage independent growth of PLC and HepG2 cells. RanBPM inactivation and reduced Gli1 expression in PLC/PRF/5 cells could be detected 8 days after siRNA transfection (FIGS. 11A &11B). The control siRNA transfection was from Ambion. After siRNA transfection, $1 \times 10^4$ cells in 1 ml of 0.4% noble agar/DMEM with 10% FBS were overlaid onto 2 ml of 0.5% bacto agar/DMAM with 10% FBS in a 6-well plate. Colonies were visualized 14 days later by 0.05% crystal violet blue. Each group was duplicated and the experiment was repeated twice with similar results (FIG. 11C).
Figure 11A:
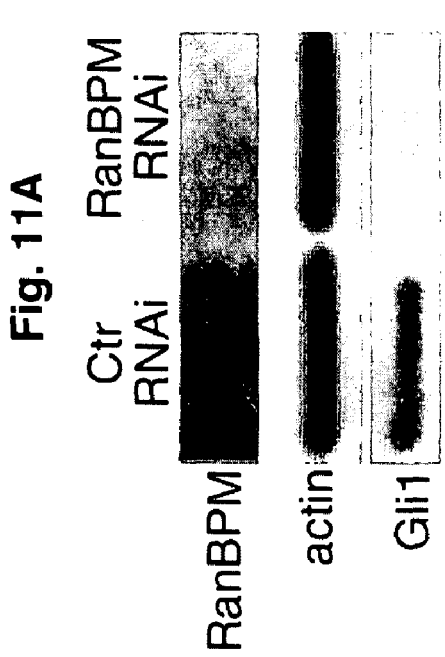
Figure 11B:
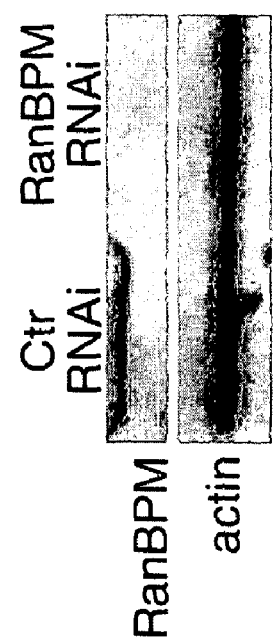

Additionally, RanBPM was inactivated by RNAi in PLC/PRF/5 (Hh signaling activated cells) cells and the anchorage independent growth of these cells in soft agar was examined. Hh signaling activation in PLC/PRF/5 cells is due to elevated expression of Shh and they are thus sensitive to Shh neutralizing antibodies or SMO antagonist cyclopamine. As a control, HepG2 cells, which have no detectable Hh signaling were used. It was observed that RanBPM expression was suppressed by the specific siRNA (is this siRNA the same as discussed supra) of RanBPM for 8 days (FIGS. 11A & 11B). The number of colonies from RanBPM siRNA-treated PLC/PRF/5 cells was significantly low than the control group [PLC/PRF/5 treated with control siRNA (p value<0.02 from student's t test), FIG. 11C]. In contrast, RanBPM did not affect colony formation of HepG2 cells (FIG. 11C).

This experiment suggests that RanBPM expression is required for growth of cancer cells with Hh signaling activation. The present invention provides additional evidence to indicate that ectopic expression of RanBPM can prevent cyclopamine-mediated apoptosis in PLC/PRF/5 cells (FIG. 12), suggesting that RanBPM functions downstream of SMO.

Example 6

Association of Hh Target Gene Expression with Loss of E-Cadherin in Pancreatic Cancer It is known that loss of E-cadherin is a marker for tumor metastasis. To understand whether Hh signaling is associated with tumor metastasis, the expression of Hh target gene PTCH1 and E-cadherin was examined in 20 pancreatic cancer specimens by immunohistochemistry (IHC). It was observed that PTCH1 was positive in 18 of the 20 tumors. Of the 18 tumors with PTCH1 expression, 17 of them had no detectable E-Cadherin, loss of which is a marker of tumor metastasis (FIG. 13). Further analysis of SMO expression indicates that a high level of SMO protein is present in 6 of 18 tumors with PTCH1 expression (FIG. 14A) and 4 tumors showed high levels of RanBPM expression (FIG. 14B).

Example 7

Hh Signaling Activation During Pancreatic Cancer Metastasis

To understand whether Hh signaling was associated with pancreatic tumor metastasis, an orthotopic mouse model of pancreatic cancer was established using ASPC1 cells. First, GFP-expressing ASPC-1 cells were injected into the pancreas of Nu/Nu mice. 6-8 weeks later, the tumor metastasis was monitored using the whole-body imaging system. When tumor metastasis was evident in the imaging system, the tumors (GFP positive) from pancreas, lymph node and liver were collected and a real-time PCR analysis of Hh target genes Gli1 and PTCH1 was performed (data from Gli1 was shown in FIG. 15, PTCH1 had a similar pattern, not shown here). It was observed that Gli1 and PTCH1 were detectable in pancreatic tumors, elevated in lymph node and further increased in liver metastasis, suggesting that Hh signaling might play a critical role during pancreatic cancer metastasis.

To test whether elevated Hh signaling during pancreatic cancer metastasis was functionally relevant, the Gli1/2 expression was inactivated by specific siRNA by weekly intraperitoneal (IP) injection. At 8 weeks, it was observed that Gli1/2 inactivation had reduced tumor metastasis in mice (FIG. 16). The results presented herein suggest that Hh signaling was required for pancreatic cancer metastasis to lymph nodes and to the liver.

The following references were cited herein:
Athar, et al. 2004. *Cancer Res.* 64:7545-52.
Bale, A. E. 2002. *Annu Rev Genomics Hum Genet.* 3:47-65.
Bar-Peled and Raikhel 1996. *Anal Biochem* 241: 140-2.
Berman, et al. 2003. *Nature* 425:846-51.
Chen, et al. 2002a. *Genes Dev.* 16:2743-8.
Chen, et al. 2004. *Science.* 306:2257-60.
Chi, et al. 2006. *Cancer Letters* (Epub ahead of print Jan. 30), 2006.
Corbit, et al. 2005. *Nature* 437:1018-21.
Denti, et al. 2004. *Chem.* 279:13027-34.
Epstein, et al. 2001. *Med Pediatr Oncol.* 36:555-8.
Fan, et al. 2004. *Endocrinology.* 145:3961-70.
Fan, et al. 2004. *Nat Genet.* 36:989-93.
Goodrich, et al. 1997. *Science.* 277:1109-13.
Hooper, J. E., and M. P. Scott, 2005. *Nat Rev Mol Cell Biol.* 6:306-17.
Huangfu, D., and K. Anderson, 2005. *Proc Natl Acad Sci USA.* 102:11325-30.
Jia, J., C. Tong, and J. Jiang. 2003. *Genes Dev.* 17:2709-20.

Jiang, J., and G. Struhl. 1995. *Cell.* 80:563-72.
Katano, M. 2005. *Cancer Lett.* 227:99-104.
Kinzler, K. W., and B. Vogelstein. 1990. *Mol Cell Biol.* 10:634-42.
Kogerman, et al. 1999. *Nat Cell Biol.* 1:312-9.
Ma, et al. 2005. *Carcinogenesis* 26:1698-705.
Ma, et al. 2006a. *Int J Cancer.* 118:139-48.
Ma et al. 2006b. *World J Gastroenterol.* 12(25):3965-9.
Murone, et al. 1999. *Curr Biol.* 9:76-84.
Nakamura, et al. 1998. *J Cell Biol.* 143:1041-52.
Nishitani, et al. 2001. *Gene.* 272:25-33.
Nusslein-Volhard, C., and E. Wieschaus. 1980. *Nature* 287: 795-801.
Ruiz i Altaba, A. 1999. *Development* 126:3205-16.
Sheng, et al. 2006. *J Biol Chem.* 281:9-12.
Thayer, et al. 2003. *Nature* 425:851-6.
Varjosalo, M., S. P. Li, and J. Taipale. 2006. *Dev Cell* 10:177-86.
Watkins, et al. 2003. *Nature* 422:313-7.
Zhu, et al. 2003. *Genes Dev.* 17:1240-52.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

---

What is claimed is:

1. A method of inhibiting growth of a cancer cell in a subject, comprising:
   contacting the cell with effective amounts of an siRNA inhibitor of RanBPM.

2. The method of claim 1, wherein said cell is a pancreatic cancer cell, basal cell carcinoma cell, medulloblastoma cell, breast cancer cell, prostate cancer cell, gastrointestinal cancer cell or lung cancer cell.

* * * * *

SEQUENCE LISTING

<160> NUMBER OF SEQ ID NOS: 5

<210> SEQ ID NO 1
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 1
gaacaugaau agacuacca                                                19

<210> SEQ ID NO 2
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 2
ggaugccuuu agccuacuau u                                             21

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
ggtgatgtca ttggctgttg                                               20

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
ggcatcgacc acttctcctg g                                             21

<210> SEQ ID NO 5
<211> LENGTH: 19
<212> TYPE: RNA
<213> ORGANISM: Artificial Sequence

```
<220> FEATURE:
<223> OTHER INFORMATION: Synthetic oligonucleotide

<400> SEQUENCE: 5
ucacugaccu accgccaaa                                              19
```